(12) United States Patent
Kawakami et al.

(10) Patent No.: US 11,225,461 B2
(45) Date of Patent: Jan. 18, 2022

(54) COMPOUND, SUBSTRATE FOR PATTERN FORMATION, PHOTODEGRADABLE COUPLING AGENT, PATTERN FORMATION METHOD, AND TRANSISTOR PRODUCTION METHOD

(71) Applicants: NIKON CORPORATION, Tokyo (JP); Kanagawa University, Yokohama (JP)

(72) Inventors: Yusuke Kawakami, Yokohama (JP); Kazuo Yamaguchi, Yokohama (JP); Michiko Itou, Yokohama (JP)

(73) Assignees: NIKON CORPORATION, Tokyo (JP); KANAGAWA UNIVERSITY, Yokohama (JP)

( * ) Notice: Subject to any disclaimer, the term of this patent is extended or adjusted under 35 U.S.C. 154(b) by 0 days.

(21) Appl. No.: 16/524,799

(22) Filed: Jul. 29, 2019

(65) Prior Publication Data
US 2019/0352260 A1 Nov. 21, 2019

Related U.S. Application Data

(63) Continuation of application No. PCT/JP2018/002899, filed on Jan. 30, 2018.

(30) Foreign Application Priority Data

Jan. 31, 2017 (JP) .............................. JP2017-016229

(51) Int. Cl.
| | | |
|---|---|---|
| *C07D 207/404* | (2006.01) | |
| *H01L 27/12* | (2006.01) | |
| *H01L 51/00* | (2006.01) | |

(52) U.S. Cl.
CPC ........ *C07D 207/404* (2013.01); *H01L 27/127* (2013.01); *H01L 51/0011* (2013.01); *H01L 51/0014* (2013.01)

(58) Field of Classification Search
None
See application file for complete search history.

(56) References Cited

U.S. PATENT DOCUMENTS

2005/0245739 A1* 11/2005 Fukushima ........... G03F 7/0045
540/350
2006/0222865 A1 10/2006 Hoshino et al.
(Continued)

FOREIGN PATENT DOCUMENTS

| CN | 1715270 A | 1/2006 |
|---|---|---|
| EP | 1610176 A2 | 12/2005 |

(Continued)

OTHER PUBLICATIONS

International Search Report dated Apr. 17, 2018 in corresponding International Patent Application No. PCT/JP2018/002899.
(Continued)

*Primary Examiner* — Xiaoming Liu
(74) *Attorney, Agent, or Firm* — Staas & Halsey, LLP

(57) ABSTRACT

Provided is a compound represented by Formula (1).

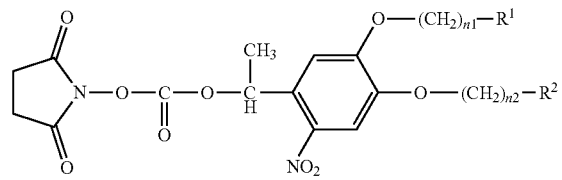

(1)

14 Claims, 3 Drawing Sheets

(56) References Cited

U.S. PATENT DOCUMENTS

2014/0240661 A1* 8/2014 Steffen ................. C09D 133/10
                                                              351/159.33
2017/0285471 A1* 10/2017 Kawakami ............ G03F 7/0751

FOREIGN PATENT DOCUMENTS

| EP | 1 736 477 A1 | 12/2006 |
|----|--------------|---------|
| JP | 4997765 | 8/2012 |
| JP | 2014-145020 | 8/2014 |

OTHER PUBLICATIONS

Written Opinion of the International Searching Authority dated Apr. 17, 2018 in corresponding International Patent Application No. PCT/JP2018/002899.
First Office Action dated Jul. 14, 2021 in Chinese Patent Application No. 201880007674.0.

* cited by examiner

COMPOUND, SUBSTRATE FOR PATTERN FORMATION, PHOTODEGRADABLE COUPLING AGENT, PATTERN FORMATION METHOD, AND TRANSISTOR PRODUCTION METHOD

CROSS-REFERENCE TO RELATED APPLICATIONS

This application is a continuation of International Application No. PCT/JP2018/002899, filed on Jan. 30, 2018, which claims priority to Japanese Patent Application No. 2017-016229, filed on Jan. 31, 2017. The disclosures of the aforementioned applications are hereby incorporated by reference in their entireties.

TECHNICAL FIELD

The present invention relates to a compound, a substrate for pattern formation, a photodegradable coupling agent, a pattern formation method, and a transistor production method.

Priority is claimed on Japanese Patent Application No. 2017-016229, filed on Jan. 31, 2017, the content of which is incorporated herein by reference.

BACKGROUND ART

Recently, in production of fine devices such as semiconductor elements, integrated circuits, and devices for organic EL displays, a method of forming patterns having different surface characteristics on a substrate to prepare a fine device using their differences in surface characteristics has been suggested.

As a pattern formation method using the differences in surface characteristics on a substrate, a method of forming a hydrophilic region and a water-repellent region on a substrate and coating the hydrophilic region with an aqueous solution containing a functional material is exemplified. According to this method, since the aqueous solution containing a functional material spread and wets only in the hydrophilic region, a thin film pattern for the functional material can be formed.

As the material which is capable of forming a hydrophilic region and a water-repellent region on a substrate, for example, PTL 1 discloses a fluorine-containing compound which is capable of changing the contact angle before and after irradiation with light. However, from the viewpoint of the environmental residue, a material that does not contain fluorine has been desired.

CITATION LIST

Patent Literature

[PTL 1] Japanese Patent No. 4997765

SUMMARY OF INVENTION

Technical Problem

According to a first embodiment of the present invention, there is provided a compound represented by Formula (1).

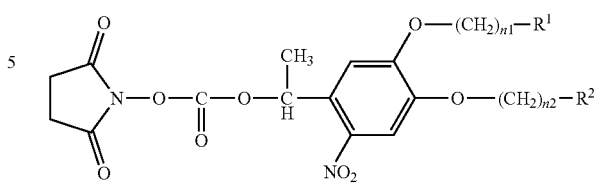

[In the formula, $R^1$ represents any one group selected from an alkyl group having 1 to 5 carbon atoms, a group represented by Formula (R2-1), and a group represented by Formula (R2-2), $R^2$ represents a group represented by Formula (R2-1) or (R2-2), n1 represents an integer of 0 to 5, and n2 represents a natural number of 1 to 5.]

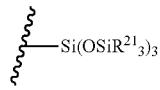

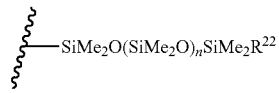

[In the formulae, $R^{21}$ and $R^{22}$ each independently represent an alkyl group having 1 to 5 carbon atoms, n represents a natural number, and the wavy line represents a bonding site.]

According to a second embodiment of the present invention, there is provided a substrate for pattern formation, which has a surface chemically modified by the compound according to the first embodiment of the present invention.

According to a third embodiment of the present invention, there is provided a photodegradable coupling agent which is formed of the compound according to the first embodiment of the present invention.

According to a fourth embodiment of the present invention, there is provided a pattern formation method of forming a pattern on a surface of an object to be treated, including: a step of aminating at least a part of the surface of the object to be treated to form an aminated surface; a step of chemically modifying the aminated surface using the compound according to the first embodiment of the present invention; a step of irradiating the chemically modified surface to be treated with light in a predetermined pattern to generate a latent image formed of a hydrophilic region and a water-repellent region; and a step of disposing a pattern forming material in the hydrophilic region or the water-repellent region.

According to a fifth embodiment of the present invention, there is provided a pattern formation method of forming a pattern on a surface of an object to be treated, including: a step of aminating at least a part of the surface of the object to be treated to form an aminated surface; a step of chemically modifying the aminated surface using the compound according to the first embodiment of the present invention; a step of irradiating the chemically modified surface to be treated with light in a predetermined pattern to generate a latent image formed of a hydrophilic region and a water-repellent region; and a step of disposing a catalyst for electroless plating in the hydrophilic region and performing electroless plating.

According to a sixth embodiment of the present invention, there is provided a transistor production method of producing a transistor which includes a gate electrode, a source electrode, and a drain electrode, the method including: a step of forming at least one electrode among the gate electrode, the source electrode, and the drain electrode using the pattern formation method according to the fourth embodiment or the fifth embodiment.

DESCRIPTION OF EMBODIMENTS

<Compound>

Figure 1:
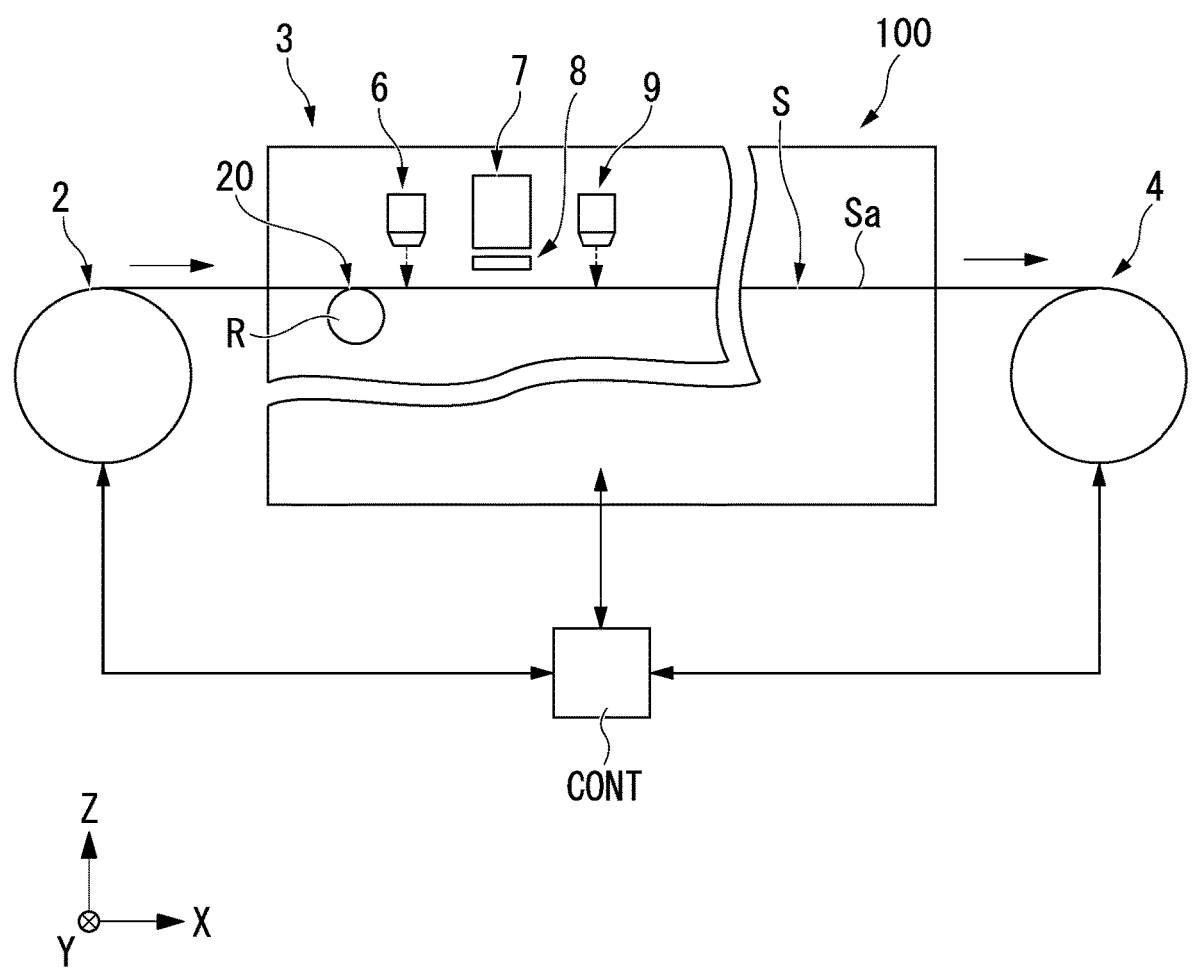
FIG. 1 is a schematic view illustrating the overall configuration of a substrate treatment device.

A first embodiment of the present invention relates to a compound represented by Formula (1). The compound according to the present embodiment contains a siloxane-based water-repellent group. In a case where a surface of an object such as a substrate is modified using the compound according to the present embodiment, the surface of the object can be reformed to be water repellent. Further, in a case where the surface thereof is irradiated with light after modification, a water-repellent group is desorbed to generate a hydrophilic group so that the surface of the object can be reformed to be hydrophilic.

It is considered that the compound according to the present embodiment can be replaced with a fluorine-based compound which has been used for reforming an object to be water repellent and is capable of exhibiting water repellency or releasability specific to a siloxane-based water-repellent group.

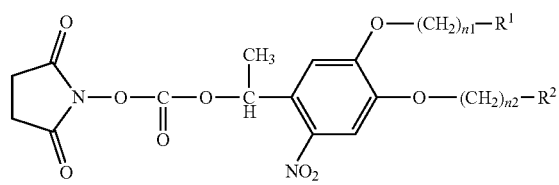

(1)

[In the formula, $R^1$ represents any one group selected from an alkyl group having 1 to 5 carbon atoms, a group represented by Formula (R2-1), and a group represented by Formula (R2-2), $R^2$ represents a group represented by Formula (R2-1) or (R2-2), n1 represents an integer of 0 to 5, and n2 represents a natural number of 1 to 5.]

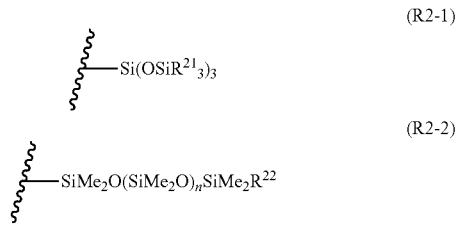

[In the formulae, $R^{21}$ and $R^{22}$ each independently represent an alkyl group having 1 to 5 carbon atoms, and n represents a natural number. The wavy line represents a bonding site]

{R1}

In Formula (1), $R^1$ represents any one group selected from an alkyl group having 1 to 5 carbon atoms, a group represented by Formula (R2-1), and a group represented by Formula (R2-2).

Examples of the alkyl group having 1 to 5 carbon atoms as $R^1$ include a methyl group, an ethyl group, a propyl group, an isopropyl group, an n-butyl group, an isobutyl group, a tert-butyl group, a pentyl group, an isopentyl group, and a neopentyl group. Among these, a methyl group or an ethyl group is preferable, and a methyl group is more preferable.

{n1 and n2}

In Formula (1), n1 represents an integer of 0 to 5. In a case of being disubstituted described below, it is preferable that n1 represents a natural number of 1 to 5, more preferably 2 to 4, and particularly preferably 3. In a case of being monosubstituted, it is preferable that n1 represents 0. n2 represents a natural number of 1 to 5, preferably 2 to 4, and more preferably 3.

{Group Represented by Formula (R2-1) or (R2-2)}

In Formula (1), examples of the group represented by $R^1$ and $R^2$ include a group represented by Formula (R2-1) or (R2-2).

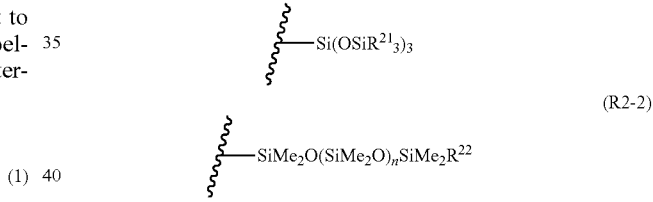

[In the formulae, $R^{21}$ and $R^{22}$ each independently represent an alkyl group having 1 to 5 carbon atoms, and n represents a natural number. The wavy line represents a bonding site.]

In Formula (R2-1) or (R2-2), $R^{21}$ and $R^{22}$ each independently represent an alkyl group having 1 to 5 carbon atoms. Examples of the alkyl group having 1 to 5 carbon atoms include groups represented by $R^1$. Among these, a methyl group, an isopropyl group, or a tert-butyl group is preferable. n in Formula (R2-2) represents a natural number, preferably 1 to 200, preferably 1 to 150, and more preferably 1 to 120.

In the description below, in a case of having a group represented by Formula (R2-1) as a group represented by $R^1$ or $R^2$, this is described as "branched" in some cases. Further, in a case of having a group represented by Formula (R2-2) as a group represented by $R^1$ or $R^2$, this is described as "linear" in some cases. Further, in a case where $R^1$ represents an alkyl group, this is described as "monosubstituted" in some cases. Further, in a case where $R^1$ represents a group represented by Formula (R2-1) or (R2-2), this is described as "disubstituted" in some cases.

The compound represented by Formula (1) according to the present embodiment includes a monosubstituted branched compound, a monosubstituted chain-like compound, a disubstituted branched compound, and a disubstituted chain-like compound by adjusting the group to be introduced into R¹ or R². From the viewpoint of further improving the contact angle of the surface of the object with water in a case of being used as a surface treatment agent or a coupling agent, a branched compound is preferable, a chain-like compound is more preferable, and a disubstituted chain-like compound is particularly preferable.

Hereinafter, specific examples of the compound represented by Formula (1) will be described below.

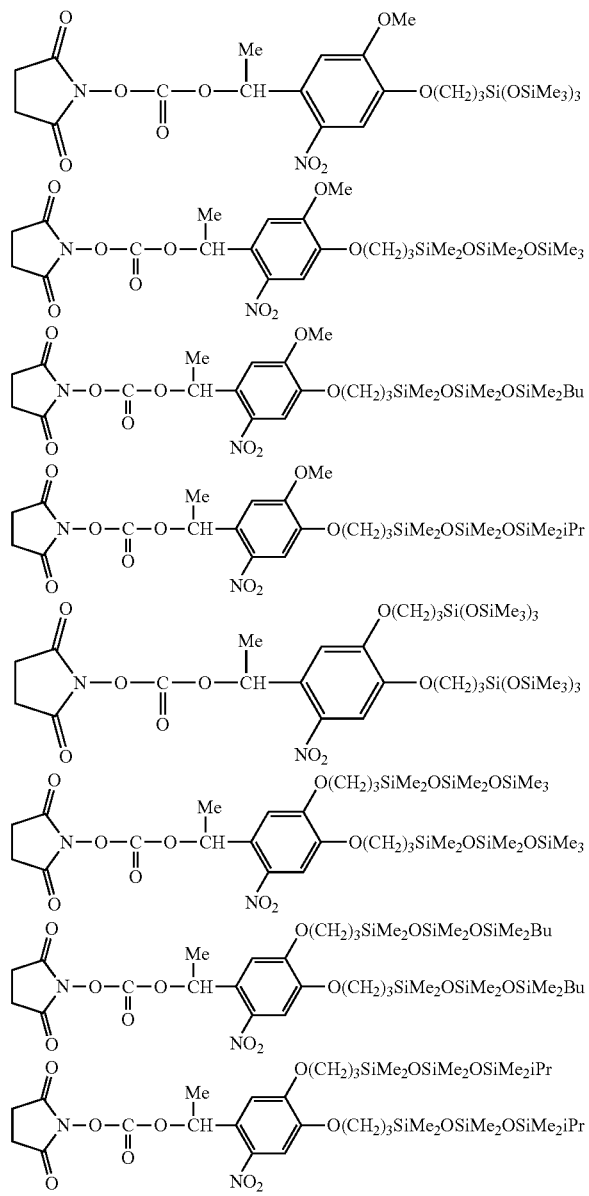

<<Method of Producing Compound>>

The compound represented by Formula (1) according to the present embodiment can be produced using the following method.

In the description of the production method below, the descriptions related to $R^1$, $R^{21}$, and $R^{22}$ are the same as described above.

[Production Method 1]

A monosubstituted chain-like compound represented by Formula (1) can be obtained by reacting a siloxane compound with an intermediate compound 14 represented by the following formula. The intermediate compound 14 may be produced using a method described in the examples below or may be synthesized using a method described in H. Nakayama et al., Colloids Surf. B, 2010, 76, p. 88 to 97.

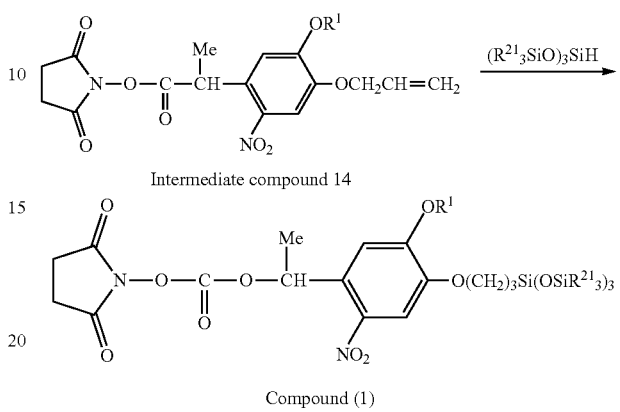

[In the formulae, $R^1$ and $R^{21}$ each independently represent an alkyl group having 1 to 5 carbon atoms.]

[Production Method 2]

A monosubstituted linear compound represented by Formula (1) can be produced using the following method. Specifically, an intermediate compound 15 is obtained by reacting a siloxane compound with an intermediate compound 13 represented by the following formula.

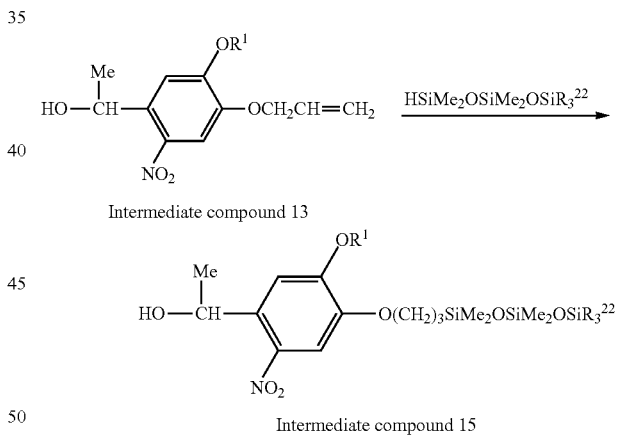

[In the formulae, $R^1$ and $R^{22}$ each independently represent an alkyl group having 1 to 5 carbon atoms.]

A compound represented by Formula (1) can be obtained by reacting succinimidyl carbonate with the obtained intermediate compound 15.

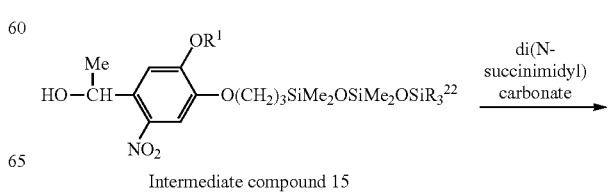

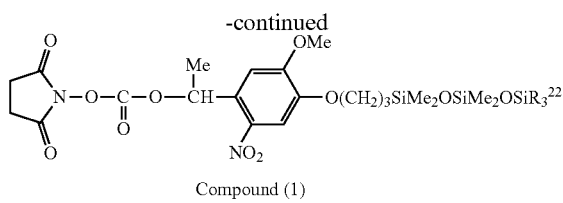

Compound (1)

[In the formulae, $R^1$ and $R^{22}$ each independently represent an alkyl group having 1 to 5 carbon atoms.]

[Production Method 3]

A disubstituted compound represented by Formula (1) can be produced using the following method. Specifically, a compound represented by Formula (1) can be obtained by reacting each siloxane compound with an intermediate compound 25 represented by the following formula.

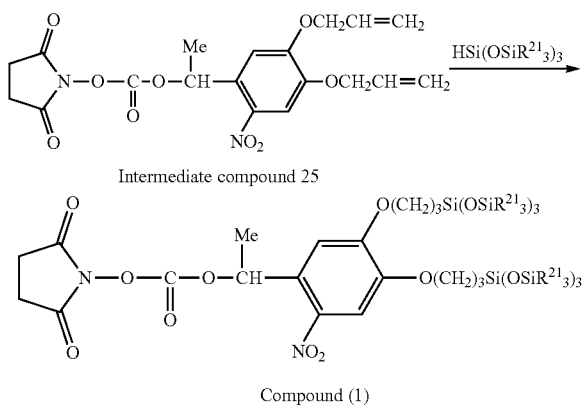

Compound (1)

[In the formulae, $R^1$ and $R^{21}$ each independently represent an alkyl group having 1 to 5 carbon atoms.]

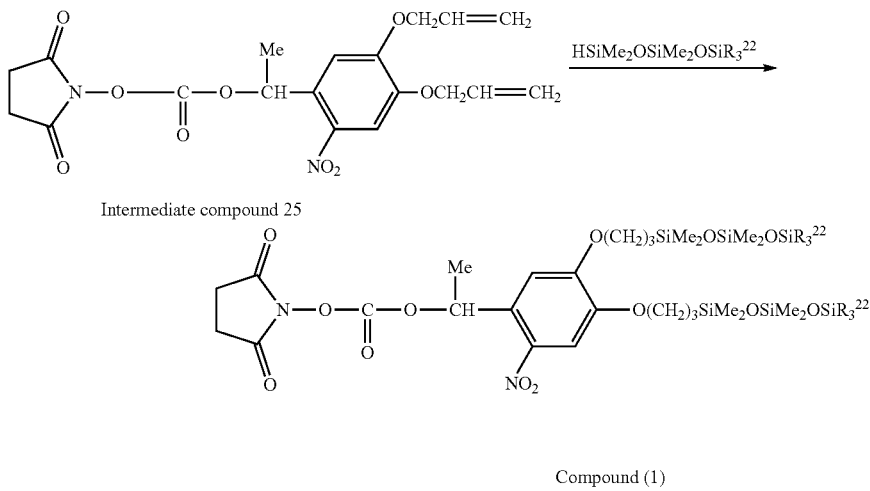

Compound (1)

[In the formulae, $R^1$ and $R^{22}$ each independently represent an alkyl group having 1 to 5 carbon atoms.]

<Substrate for Pattern Formation>

A second embodiment of the present invention relates to a substrate for pattern formation which has a surface chemically modified using the compound according to the first embodiment.

The substrate for pattern formation according to the present embodiment has a surface modified using the compound according to the first embodiment. Therefore, by selectively exposing the substrate through a mask or the like, a hydrophilic region is formed in an exposed portion and a water-repellent region is formed in an unexposed portion on the substrate for pattern formation.

By coating the substrate on which a hydrophilic region and a water-repellent region are formed with a pattern forming material, the hydrophilic region formed in the exposed portion can be selectively coated with the pattern forming material, and thus metal wiring and the like can be formed.

The base material is not particularly limited, and preferred examples thereof include glass, quartz glass, a silicon wafer, a plastic plate, and a metal plate. Further, a substrate on which a metal thin film is formed may be used on these substrates.

The shape of the base material is not particularly limited, and a flat surface, a curved surface, or a flat surface which is partially curved is preferable, and a flat surface is more preferable. Further, the area of the base material is not particularly limited, and a base material having a surface with a size as large as a coating method of the related art can be applied can be employed. Further, it is preferable that the surface chemically modified using the compound according to the first embodiment is formed on one flat surface of a base material on the plane.

In a case where a surface of a substrate is modified, it is preferable that the surface of the substrate is subjected to a pre-treatment in advance. As the pre-treatment method, a pre-treatment carried out using a piranha solution or a pre-treatment using a UV-ozone cleaner is preferable.

<Photodegradable Coupling Agent>

A third embodiment of the present invention relates to a photodegradable coupling agent formed of the compound according to the first embodiment.

The photodegradable coupling agent according to the present embodiment includes a photodegradable group containing a liquid-repellent group, and an adhesion group linked to the photodegradable group through a functional group, in which the liquid-repellent group has a siloxane structure, and the functional group becomes a residue of an amino group after photodegradation. Therefore, the photodegradable coupling agent according to the present embodiment is capable of greatly ensuring a difference in contact angle before and after the irradiation with light.

<Pattern Formation Method>

A fourth embodiment of the present invention relates to a pattern formation method of forming a pattern on a surface of an object to be treated, and the method includes a step of aminating the surface of the object to be treated to produce an aminated surface; a step of chemically modifying the aminated surface using the compound according to the first embodiment; a step of irradiating the chemically modified surface to be treated with light in a predetermined pattern to generate a latent image formed of a hydrophilic region and a water-repellent region; and a step of disposing a pattern forming material in the hydrophilic region or the water-repellent region.

[Amination Step]

According to the pattern formation method according to the present embodiment, first, the surface of the object to be treated is aminated to produce an aminated surface. In the present step, a substrate containing an amino group is produced by acting 3-aminopropyltrimethoxysilane on a substrate containing a hydroxyl group as described below.

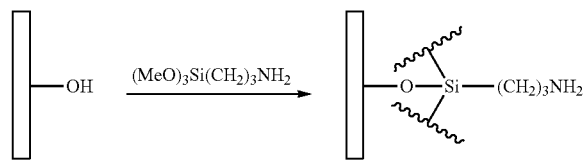

[Chemical Modification Step]

The present step is a step of chemically modifying the aminated surface to be treated using the compound according to the first embodiment in the pattern formation method of forming a pattern on the surface of the object to be treated.

The object is not particularly limited, and examples thereof include a metal, a crystalline material (such as a monocrystalline material, a polycrystalline material, and a partially crystalline material), an amorphous material, a conductor, a semiconductor, an insulator, an optical element, a coated substrate, fibers, glass, ceramics, zeolite, plastic, thermosetting and thermoplastic materials (such as polyacrylate, polycarbonate, polyurethane, polystyrene, a cellulose polymer, polyolefin, polyamide, polyamide, a resin, polyester, and polyphenylene which are occasionally doped), a film, a thin film, and foil.

In the pattern formation method according to the present embodiment, it is preferable that a circuit pattern for an electronic device is formed on a flexible substrate.

In the present embodiment, for example, a resin film or foil such as stainless steel can be used as the flexible substrate serving as an object. Examples of the resin film include materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin.

Here, the flexibility indicates a property in which the substrate can be bent without being cut or fractured even in a case where a force with a degree of the own weight of the substrate is applied to the substrate. Further, the concept of the flexibility also includes a property in which the substrate is bent by a force with a degree of the own weight of the substrate. Further, the flexibility varies depending on the material of the substrate, the size, the thickness, or the environment such as the temperature. In addition, as a substrate, a single strip-shaped substrate may be used or a substrate having a configuration in which a plurality of unit substrates are connected to be formed into a strip shape may be used.

In the present step, it is preferable that the entire surface of the object to be treated or a specific region is chemically modified using the compound according to the first embodiment.

A method of chemically modifying the surface of the object to be treated is not particularly limited as long as the carbonate group in Formula (1) is bonded to the substrate, and a known method such as an immersion method or a chemical treatment method can be used.

An example of chemical modification in the present step will be described.

The chemical modification in the present step can be performed by, for example, reacting the compound represented by Formula (1) with the substrate containing an amino group which has been produced in a pre-step as described below.

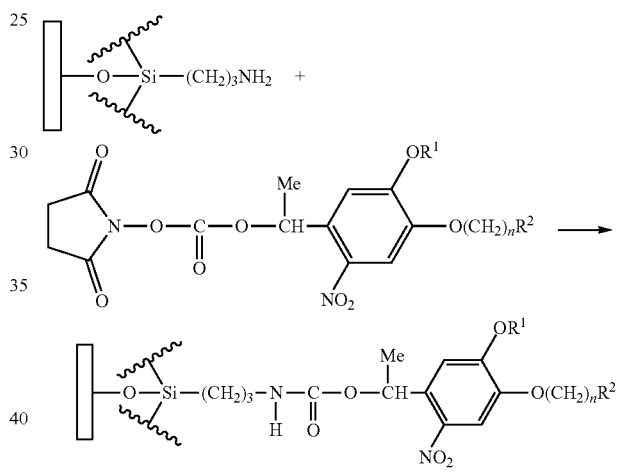

[In the formulae, $R^1$ and $R^{21}$ each independently represent an alkyl group having 1 to 5 carbon atoms. n represents a natural number of 1 to 5.]

[Latent Image Generation Step]

The present step is a step of exposing the chemically modified surface to be treated and generating a latent image formed of a hydrophilic region and a water-repellent region.

As light to be applied at the time of exposure, ultraviolet rays are preferable. It is preferable that the light to be applied includes light having a wavelength of 200 nm to 450 nm and more preferable that the light to be applied includes light having a wavelength of 320 nm to 450 nm. Further, it is also preferable that light that includes light having a wavelength of 365 nm is applied. The light having these wavelengths can efficiently degrade a photodegradable group. Examples of the light source include a low-pressure mercury lamp, a high-pressure mercury lamp, an ultrahigh-pressure mercury lamp, a xenon lamp, and a sodium lamp; a gas laser such as nitrogen, a liquid laser of an organic dye solution, and a solid-state laser obtained by allowing an inorganic single crystal to contain rare earth ions.

As a light source other than the laser from which monochromatic light is obtained, light having a specific wavelength, in which a broadband line spectrum or a continuous spectrum is extracted using an optical filter such as a band pass filter or a cutoff filter, may be used. From the viewpoint that a large area can be irradiated at once, a high-pressure mercury lamp or an ultrahigh-pressure mercury lamp is preferable as a light source.

According to the pattern formation method of the present embodiment, light can be optionally applied within the above-described range, but it is preferable that light energy showing distribution particularly corresponding to a circuit pattern is applied.

In the present step, since a group having water-repellent performance is desorbed and a residue (amino group) having hydrophilic performance is generated by irradiating the chemically modified surface to be treated with light in a predetermined pattern, a latent image formed of a hydrophilic region and a water-repellent region can be generated after the irradiation with light.

In the present step, it is preferable that a latent image having a circuit pattern due to a difference between hydrophilicity and water repellency is generated on a surface of a flexible substrate.

By irradiating the chemically modified surface to be treated with light in a predetermined pattern, a group having water-repellent performance is desorbed as shown below, and a residue (amino group) having hydrophilic performance is generated.

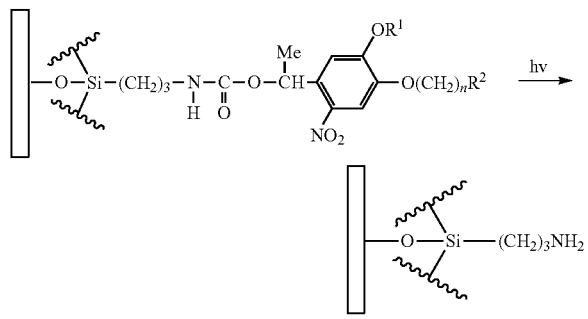

[In the formulae, $R^1$ and $R^{21}$ each independently represent an alkyl group having 1 to 5 carbon atoms. n represents a natural number of 1 to 5.]

[Step of Disposing Pattern Forming Material]

The present step is a step of disposing a pattern forming material in the hydrophilic region or water-repellent region generated in the step described above.

Examples of the pattern forming material include a wiring material (metal solution) obtained by dispersing particles of gold, silver, copper, alloys of these, or the like in a predetermined solvent, a precursor solution containing the above-described metals, an electronic material obtained by dissolving an insulator (resin), a semiconductor, an organic EL light emitting material, or the like in a predetermined solvent, and a resist solution.

According to the pattern formation method of the present embodiment, it is preferable that the pattern forming material is a conductive material, a semiconductor material, or an insulating material.

As the conductive material, a pattern forming material formed of a dispersion liquid obtained by dispersing conductive fine particles in a dispersion medium is exemplified. As the conductive fine particles, for example, metal fine particles containing any of gold, silver, copper, palladium, nickel, and ITO, oxides of these, conductive polymers, and fine particles of a superconductor are used.

These conductive fine particles can be used by coating the surface thereof with an organic substance in order to improve the dispersibility.

The dispersion medium is not particularly limited as long as the above-described conductive fine particles can be dispersed in the dispersion medium and aggregation did not occur. Examples of the dispersion medium include water; alcohols such as methanol, ethanol, propanol, and butanol; hydrocarbon-based compounds such as n-heptane, n-octane, decane, dodecane, tetradecane, toluene, xylene, cymene, durene, indene, dipentene, tetrahydronaphthalene, decahydronaphthalene, and cyclohexylbenzene; ether-based compounds such as ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, 1,2-dimethoxyethane, bis(2-methoxyethyl)ether, and p-dioxane; and polar compounds such as propylene carbonate, γ-butyrolactone, N-methyl-2-pyrrolidone, dimethylformamide, dimethyl sulfoxide, and cyclohexanone. Among these, from the viewpoints of the dispersibility of fine particles, stability of the dispersion liquid, and ease of application to a liquid droplet discharging method (ink jet method), water, alcohols, hydrocarbon-based compounds, and ether-based compounds are preferable. As the dispersion medium, water and hydrocarbon-based compounds are more preferable.

As the semiconductor material, an organic semiconductor material formed of a dispersion liquid obtained by dispersing or dissolving the material in a dispersion medium can be used. As the organic semiconductor material, a polymer material or a low-molecular weight material of a π electron conjugated system in which the skeleton thereof is formed of a conjugated double bond is desirable. Typical examples thereof include soluble low-molecular weight materials, for example, acenes such as pentacene, and thienoacenes such as benzothienobenzothiophene; and soluble polymer materials such as polythiophene, poly(3-alkylthiophene), and a polythiophene derivative. Further, a soluble precursor material which is changed to the above-described semiconductor through a heat treatment may be used, and examples of the pentacene derivative include sulfinylacetamide pentacene. In addition, the semiconductor material is not limited to the organic semiconductor materials, and inorganic semiconductor materials may be used.

Examples of the insulating material include insulating materials formed of a dispersion medium obtained by dispersing or dissolving polyimide, polyamide, polyester, acryl, PSG (phosphorus glass), BPSG (phosphorus boron glass), polysilazane-based SOG, silicate-based SOG (spin on glass), alkoxy silicate-based SOG, $SiO_2$ having a Si—CH3 bond represented by a siloxane polymer, or the like in a dispersion medium.

In the present step, as a method of disposing the pattern forming material, a liquid droplet discharging method, an ink jet method, a spin coat method, a roll coat method, a slot coat method, a dip coat method, or the like can be employed.

Hereinafter, the pattern formation method according to the present embodiment will be described with reference to the accompanying drawings.

According to the pattern formation method of the present embodiment, in a case where a flexible substrate compatible with a so-called roll-to-roll process is used, a pattern may be formed using a substrate treatment device 100 which is a roll-to-roll device as illustrated in FIG. 1.

The configuration of the substrate treatment device 100 is illustrated in FIG. 1.

As illustrated in FIG. 1, the substrate treatment device 100 includes a substrate supply unit 2 which supplies a stripe-shaped substrate (for example, a stripe-shaped film member) S; a substrate treatment unit 3 which performs a treatment on a surface (surface to be treated) Sa of the substrate S; a substrate recovery unit 4 which recovers the substrate S; a coating unit 6 which applies the compound according to the first embodiment; an exposure unit 7; a mask 8; a patterned material coating unit 9; and a control unit CONT which controls each unit. The substrate treatment unit 3 can perform various treatments on the surface of the substrate S between the time at which the substrate S is sent out from the substrate supply unit 2 and the time at which the substrate S is recovered by the substrate recovery unit 4.

The substrate treatment device 100 can be suitably used in a case where a display element (electronic device) such as an organic EL element or a liquid crystal display element is formed on the substrate S.

Further, FIG. 1 illustrates a system of using a photomask for generating light having a desired pattern, but the present embodiment can also be suitably applied to a maskless exposure system that does not use a photomask. Examples of the maskless exposure system of generating patterned light without using a photomask include a method of using a spatial light modulation element such as DMD, and a system of scanning spot light such as a laser beam printer.

The pattern formation method according to the present embodiment will be described appropriately using an XYZ coordinate system after the XYZ coordinate system is set as illustrated in FIG. 1. In the XYZ coordinate system, for example, an X axis and a Y axis are set along the horizontal plane, and a Z axis is set upward along the vertical direction. Further, the overall substrate treatment device 100 is along the X axis, and the substrate S is transported from a negative side (− side) to a positive side (+ side). At this time, the width direction (short length direction) of the stripe-shaped substrate S is set as the Y axis direction.

As the substrate S to be treated in the substrate treatment device 100, for example, a resin film or foil such as stainless steel can be used. Examples of the resin film include materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin.

It is preferable that the thermal expansion coefficient of the substrate S is small so that the size thereof is not changed even in a case of being heated at approximately 200° C. The thermal expansion coefficient can be decreased by mixing an inorganic filler into a resin film. Examples of the inorganic filler include titanium oxide, zinc oxide, alumina, and silicon oxide. Further, the substrate S may be single ultrathin glass having a thickness of 100 µm which has been produced by a float glass method or the like or a laminate obtained by bonding a resin film or aluminum foil to this ultrathin glass.

The substrate S is formed such that the size thereof in the width direction (short length direction) is in a range of 1 m to 2 m and the size thereof in the length direction (long length direction) is 10 m or longer. These dimensions are merely an example and are not limited thereto. For example, the size of the substrate S in the Y direction may be 50 cm or shorter or 2 m or longer. Further, the size of the substrate S in the X direction may be 10 m or shorter.

It is preferable that the substrate S is formed to have a flexibility. Here, the flexibility indicates a property in which the substrate can be bent without being cut or fractured even in a case where a force with a degree of the own weight of the substrate is applied to the substrate. Further, the concept of the flexibility also includes a property in which the substrate is bent by a force with a degree of the own weight of the substrate.

Further, the flexibility varies depending on the material of the substrate, the size, the thickness, or the environment such as the temperature. In addition, as a substrate S, a single strip-shaped substrate may be used or a substrate having a configuration in which a plurality of unit substrates are connected to be formed into a strip shape may be used.

The substrate supply unit 2 sends and supplies the substrate S wound in a roll shape to the substrate treatment unit 3. In this case, a shaft that winds the substrate S, a rotary driving device that rotates the shaft, and the like are provided in the substrate supply unit 2. In addition, a configuration in which a cover portion that covers the substrate S in a state of being wound in a roll shape is provided may be employed. Further, the substrate supply unit 2 is not limited to the mechanism of sending out the substrate S wound in a roll shape and may have a mechanism (for example, a nip type driving roller) of sequentially sending out the stripe-shaped substrate S in the length direction thereof.

The substrate recovery unit 4 recovers the substrate S having passed through the substrate treatment device 100 by means of winding the substrate S, for example, in a roll shape. Similar to the substrate supply unit 2, the substrate recovery unit 4 is provided with a shaft for winding the substrate S, a rotary driving source that rotates the shaft, a cover portion that covers the recovered substrate S, and the like. Further, in a case where the substrate S in the substrate treatment unit 3 is cut into a panel shape, for example, the substrate is recovered in a state of being overlapped. In other words, a configuration in which the substrate S is recovered in a state different from the state in which the substrate S is wound in a roll shape may be employed.

The substrate treatment unit 3 performs a step of transporting the substrate S supplied from the substrate supply unit 2 to the substrate recovery unit 4 and chemically modifying the surface Sa of the substrates S to be treated using the compound according to the first embodiment during the process of transportation; a step of irradiating the chemically modified surface to be treated with light in a predetermined pattern; and a step of disposing the pattern forming material. The substrate treatment unit 3 includes a compound coating unit 6 which coats the surface Sa of the substrate S to be treated with the compound according to the first embodiment; an exposure unit 7 which irradiates the surface with light; a mask 8; a patterned material coating unit 9; and a transport device 20 which includes a driving roller R and the like for sending the substrate S under conditions compatible with the form of the processing treatment.

As the compound coating unit 6 and the patterned material coating unit 9, liquid droplet coating devices (such as a liquid droplet discharge type coating device, an ink jet type coating device, a spin coat type coating device, a roll coat type coating device, and a slot coat type coating device) are exemplified.

Each of these devices is appropriately provided along the transport path of the substrate S, and a panel and the like of a flexible display can be produced using a so-called roll-to-roll system. In the present embodiment, the exposure unit 7 is provided and a device that performs steps (a photosensitive layer formation step, a photosensitive layer development step, and the like) before and after the steps described above is provided inline as necessary.

<Wiring Pattern Formation Method Using Electroless Plating>

A fifth embodiment of the present invention relates to a pattern formation method of forming a pattern on the surface of the object to be treated, and the method includes a step of aminating at least a part of the surface of the object to be treated to form an aminated surface; a step of chemically modifying the aminated surface using the compound according to the first embodiment; a step of irradiating the chemically modified surface to be treated with light in a predetermined pattern to generate a latent image formed of a hydrophilic region and a water-repellent region; and a step of disposing a catalyst for electroless plating in the hydrophilic region and performing electroless plating.

Figure 2:
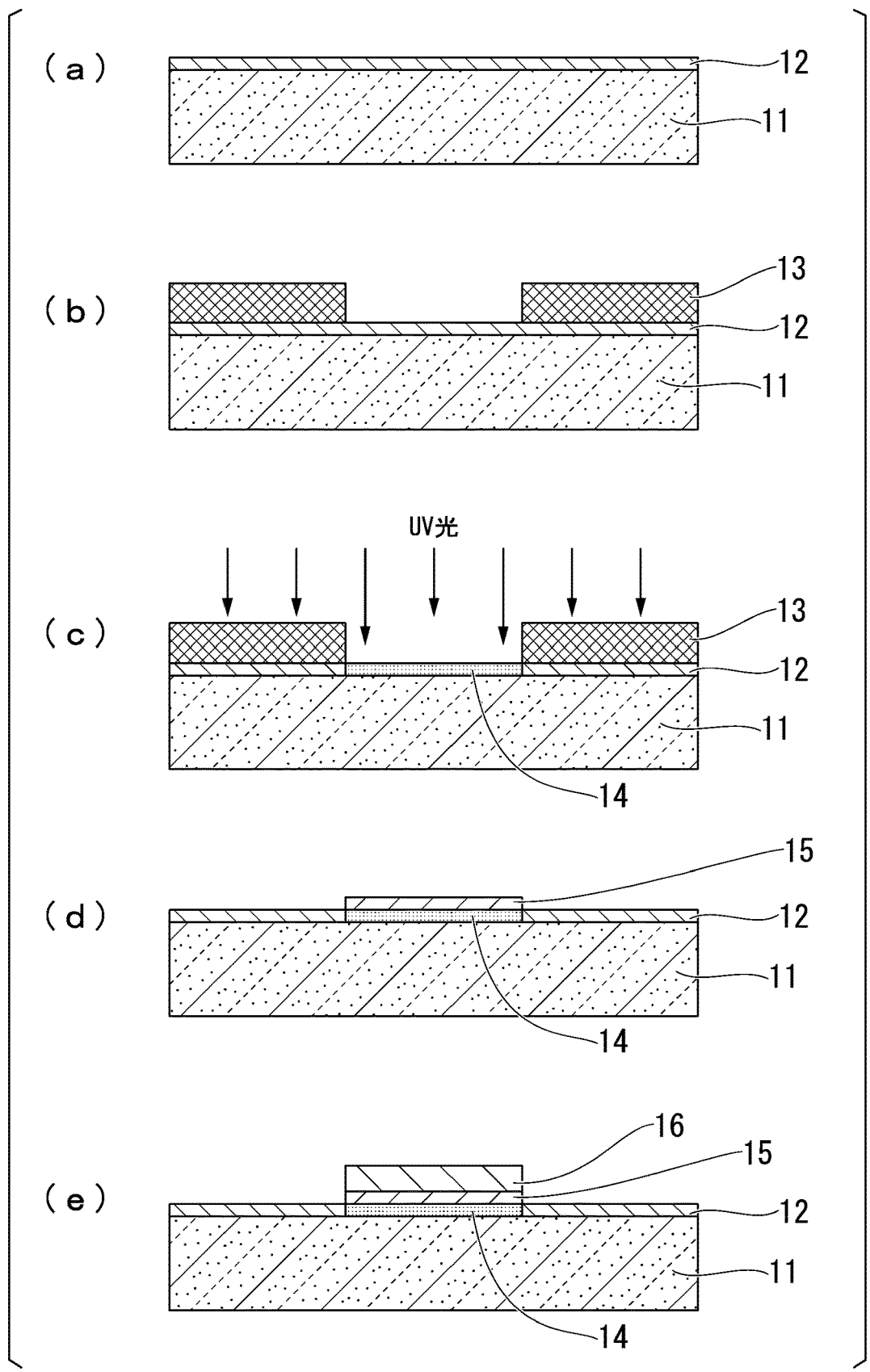
FIG. 2 is a view schematically illustrating steps of a pattern formation method.

According to the present embodiment, for example, a wiring pattern can be formed using electroless plating according to the following method. Hereinafter, the description will be made with reference to FIG. 2.

(First Step)

First, as illustrated in FIG. 2(a), a compound layer 12 is formed by aminating a surface of a substrate 11 and coating the surface with the compound according to the first embodiment.

As the coating method, any typical film formation technique such as a physical vapor deposition (PVD) method, a chemical vapor deposition (CVD) method, and a liquid phase growth method may be used. Among these, a liquid phase growth method is preferable, and examples of the liquid phase growth method include a coating method (spin coating, dip coating, die coating, spray coating, roll coating, or brush coating) and a printing method (flexographic printing or screen printing). Further, a SAM film or an LB film may be formed.

Further, in the present step, a treatment for drying a solvent through heat or pressure reduction may be carried out.

(Second Step)

Next, as illustrated in FIG. 2(b), a photomask 13 having an exposed region with a predetermined pattern is prepared. The exposure method is not limited to means for using a photomask, and means such as projection exposure using an optical system such as a lens or a mirror or maskless exposure using a spatial light modulation element or laser beams can be used. Further, the photomask 13 may be provided so as to be in contact with the compound layer 12 or provided so as not to be in contact with the compound layer 12.

(Third Step)

Thereafter, as illustrated in FIG. 2(c), the compound layer 12 is irradiated with UV light through the photomask 13. In this manner, the compound layer 12 is exposed in the exposed region of the photomask 13 so that a hydrophilic region 14 is formed.

Further, UV light can be radiated at a wavelength such that the optimum quantum efficiency is exhibited using the structure of a photosensitive group. Examples thereof include i-line having a wavelength of 365 nm. Further, the exposure amount and the exposure time may be set such that some amino groups are generated and complete deprotection does not necessarily proceed. At this time, in the plating step described below, the conditions (the activity of a plating bath or the like) according to the progress of deprotection can be appropriately changed.

(Fourth Step)

Next, as illustrated in FIG. 2(d), a catalyst for electroless plating is applied to the surface to form a catalyst layer 15. The catalyst for electroless plating is a catalyst that reduces metal ions contained in a plating solution for electroless plating, and examples thereof include silver and palladium.

The surface of the hydrophilic region 14 is exposed to an amino group, and an amino group is capable of capturing and reducing the above-described catalyst for electroless plating. Therefore, the catalyst for electroless plating is captured only on the hydrophilic region 14 so that the catalyst layer 15 is formed. Further, as the catalyst for electroless plating, a catalyst which can be carried by an amino group can be used.

(Fifth Step)

As illustrated in FIG. 2(e), a plating layer 16 is formed by performing an electroless plating treatment. Further, examples of the material of the plating layer 16 include nickel-phosphorus (NiP) and copper (Cu).

In the present step, the substrate 11 is immersed in an electroless plating bath to reduce metal ions on the surface of the catalyst so that the plating layer 16 is deposited. At this time, since the catalyst layer 15 that carries a sufficient amount of the catalyst is formed on the surface of the hydrophilic region 14, the plating layer 16 can be selectively deposited only on the hydrophilic region 14. In a case of insufficient reduction, metal ions may be actively reduced by immersing the substrate 11 in a reducing agent solution such as sodium hypophosphite or sodium borohydride.

By performing the above-described step, a wiring pattern can be formed on a predetermined substrate using the compound according to the first embodiment.

<Method of Producing Transistor>

Figure 3:
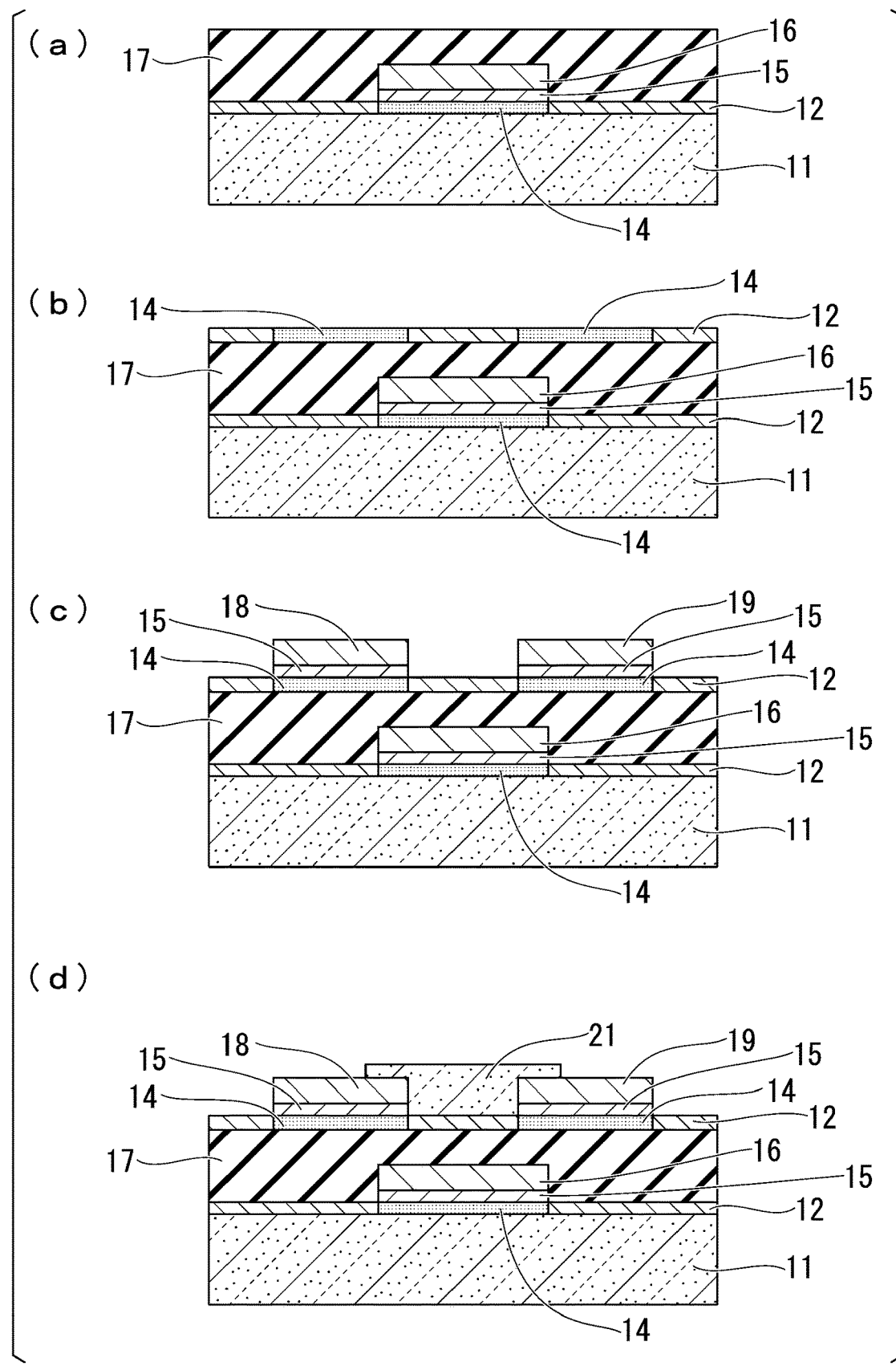
FIG. 3 is a view schematically illustrating an example of steps of a transistor production method.

Further, a transistor production method of forming the plating layer 16 obtained in the fifth step into a gate electrode will be described with reference to FIG. 3.

(Sixth Step)

As illustrated in FIG. 3(a), the compound layer 12 is covered, according to a known method, with the plating layer 16 having an electroless plating pattern formed using the above-described electroless plating pattern formation method to form an insulator layer 17 on the compound layer 12. The insulator layer 17 may be formed by coating the compound layer 12 with the coating solution obtained by dissolving one or more resins from among an ultraviolet curable acrylic resin, an epoxy resin, an ene-thiol resin, and a silicone resin in an organic solvent. The insulator layer 17 can be formed into a desired pattern by irradiating a coated film with ultraviolet rays through a mask provided with an opening portion corresponding to a region where the insulator layer 17 is formed.

(Seventh Step)

As illustrated in FIG. 3(b), the hydrophilic region 14 is formed in a portion where a source electrode and a drain electrode are formed in the same manner as in the first to third steps of the above-described electroless plating pattern formation method.

(Eighth Step)

As illustrated in FIG. 3(c), a plating layer 18 (source electrode) and a plating layer 19 (drain electrode) are formed by allowing the hydrophilic region 14 to carry the catalyst for electroless plating to form the catalyst layer 15 and performing electroless plating in the same manner as in the fourth and fifth steps of the above-described electroless plating pattern formation method. Further, examples of the material of the plating layers 18 and 19 include nickel-phosphorus (NiP) and copper (Cu), but the layers may be formed of a material different from the material of the plating layer 16 (gate electrode).

(Ninth Step)

As illustrated in FIG. 3(d), a semiconductor layer 21 is formed between the plating layer 18 (source electrode) and the plating layer 19 (drain electrode). The semiconductor layer 21 may be formed by, for example, preparing a solution obtained by dissolving an organic semiconductor material soluble in an organic solvent such as TIPS pentacene (6,13-bis(triisopropylsilylethynyl)pentacene) in the organic solvent, coating a space between the plating layer 18 (source electrode) and the plating layer 19 (drain electrode) with the solution, and drying the solution. Further, the compound layer 12 between the plating layer 18 (source electrode) and the plating layer 19 (drain electrode) may be exposed and hydrophilized before formation of the semiconductor layer 21. By hydrophilizing the portion corresponding to a channel of a transistor, the hydrophilized portion is suitably coated with the solution, and the semiconductor layer 21 tends to be selectively formed. Further, the semiconductor layer 21 may be formed by adding one or more kinds of insulating polymers such as PS (polystyrene) or PMMA (methyl polymethacrylate) to the solution, applying the solution containing the insulating polymers, and drying the solution. In this manner, in a case where the semiconductor layer 21 is formed, the insulating polymers are concentrated and formed in the lower portion of the semiconductor layer 21 (on a side of the insulator layer 17). In a case where a polar group such as an amino group is present at the interface between the organic semiconductor and the insulator layer, the transistor characteristics tend to be degraded. However, in a case where a configuration in which the organic semiconductor is provided through the above-described insulating polymers is employed, degradation of the transistor characteristics can be suppressed. In this manner, a transistor can be produced.

According to the above-described method, it is not necessary to separately provide a chemical resist and the like in the UV exposure step, and a simple step using only a photomask can be carried out. Therefore, the same applies to the step of removing the resist layer. Further, an activation treatment step of the catalyst which is usually required can be omitted due to the catalyst reduction ability of the amino group, and high-resolution patterning can be made while significant cost reduction and time reduction are realized. Further, since a dip coating method can be used, this method can also be used in the roll-to-roll step due to excellent compatibility.

Further, the structure of the transistor is not particularly limited and can be appropriately selected depending on the purpose thereof. In the forms illustrated in FIGS. 2 and 3, the method of producing a bottom contact and bottom gate type transistor has been described, but a top contact and bottom gate type transistor, a top contact and top gate type transistor, and a bottom contact and top gate type transistor may be produced in the same manner as described above. Further, in the forms illustrated in FIGS. 2 and 3, the method of forming all of the gate electrode, the source electrode, and the drain electrode using the compound according to the first embodiment has been described, but only the gate electrode may be formed using the compound according to the first embodiment or only the source electrode and the drain electrode may be formed using the compound according to the first embodiment.

EXAMPLES

Hereinafter, the present invention will be described in more detail based on the examples, but the present invention is not limited to the following examples.

<Synthesis of Compound 1a>

<<Step 1; Synthesis of 1-(4-allyloxy-3-methoxyphenyl) ethanone>>

4-Hydroxy-3-methoxyacetophenone (5.00 g, 30.1 mmol) was put into a 300 mL eggplant flask to be dissolved in acetone (50 mL), potassium carbonate (6.24 g, 45.1 mmol) was added thereto, the solution was stirred at room temperature for 5 minutes, allyl bromide (5.46 g, 45.1 mmol) was added thereto, and the resulting solution was stirred at room temperature for 24 hours. After concentration, ethyl acetate (50 mL×2) and pure water (50 mL) were added to the solution for extraction, and the organic layer was sequentially washed with a saturated sodium carbonate aqueous solution (50 mL×3) and saturated saline solution (50 mL×2), dried over anhydrous magnesium sulfate, filtered, and concentrated, thereby obtaining 6.09 g (29.5 mmol, 98%) of pale yellow oil (intermediate compound 11; 1-(4-allyloxy-3-methoxyphenyl)ethanone).

The identification result of the obtained intermediate compound 11 is described below.

$^1$H NMR (CDCl$_3$/TMS, 400 MHz): δ 2.57 (3H, s), 3.94 (3H, s), 4.69 (2H, dt, J=5.4, 1.5 Hz), 5.33 (1H, dq, J=11, 1.3 Hz), 5.43 (1H, dq, J=17, 1.5 Hz), 6.09 (1H, ddt, J=17, 11, 5.4 Hz), 6.89 (1H, d, J=9.0 Hz), 7.52-7.56 (2H, m).

Intermediate compound 11

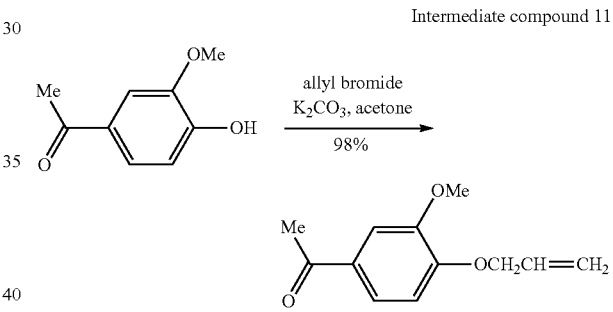

<<Step 2; Synthesis of 1-(4-allyloxy-5-methoxy-2-nitrophenyl)ethanone>>

The intermediate compound 11 (497 mg, 2.41 mmol) was put into a 50 mL eggplant flask to be dissolved in acetic acid (3 mL), fuming nitric acid (1 mL, 24.1 mmol) was slowly added dropwise thereto on an ice bath, and the solution was stirred at 0° C. for 30 minutes. Cold water (10 mL) was added to the resulting solution for extraction using ethyl acetate (10 mL×3), and the organic layer was sequentially washed with a saturated sodium bicarbonate aqueous solution (10 mL) and saturated saline solution (10 mL×2), dried over anhydrous magnesium sulfate, filtered, and concentrated. The resultant was purified by silica gel column chromatography (hexane:ethyl acetate=4:1→2:1), thereby obtaining 345 mg (1.37 mmol, 57%) of a yellowish white solid (intermediate compound 12; 1-(4-allyloxy-5-methoxy-2-nitrophenyl)ethanone).

The identification result of the obtained intermediate compound 12 is described below.

$^1$H NMR (CDCl$_3$/TMS, 400 MHz): δ 2.50 (3H, s), 3.98 (3H, s), 4.71 (2H, dt, J=5.5, 1.4 Hz), 5.39 (1H, dq, J=11, 1.3 Hz), 5.48 (1H, dq, J=17, 1.3 Hz), 6.07 (1H, ddt, J=17, 11, 5.4 Hz), 6.76 (1H, s), 7.62 (1H, s).

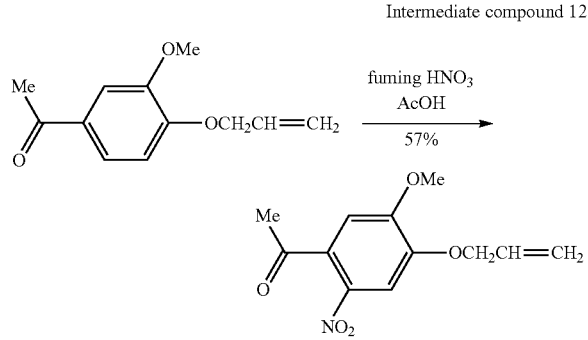

Intermediate compound 12

<<Step 3; Synthesis of 1-(4-allyloxy-5-methoxy-2-nitrophenyl)ethanol>>

The intermediate compound 12 (1.41 g, 5.61 mmol) obtained in the above-described step, tetrahydrofuran (10 mL), and methanol (10 mL) were put into a 50 mL eggplant flask, and sodium borohydride (637 mg, 16.8 mmol) was slowly added thereto on an ice bath. The solution was stirred at 0° C. for 20 minutes and further stirred at room temperature for 40 minutes. After concentration, chloroform (10 mL×3) and pure water (30 mL) were added to the resulting solution for extraction, and the organic layer was washed with saturated saline solution (20 mL×3), dried over anhydrous magnesium sulfate, filtered, and concentrated, thereby obtaining 1.40 g (5.54 mmol, 99%) of a yellowish white solid (intermediate compound 13; 1-(4-allyloxy-5-methoxy-2-nitrophenyl)ethanol).

The identification result of the obtained intermediate compound 13 is described below.

$^1$H NMR (CDCl$_3$/TMS, 400 MHz): δ 1.56 (3H, d, J=6.3 Hz), 2.29 (1H, d, J=3.7 Hz), 4.00 (3H, s), 4.67 (2H, dt, J=5.5, 1.4 Hz), 5.36 (1H, dq, J=11, 1.3 Hz), 5.46 (1H, dq, J=17, 1.5 Hz), 5.57 (1H, qd, J=6.3, 3.7 Hz), 6.07 (1H, ddt, J=17, 11, 5.4 Hz), 7.31 (1H, s), 7.59 (1H, s).

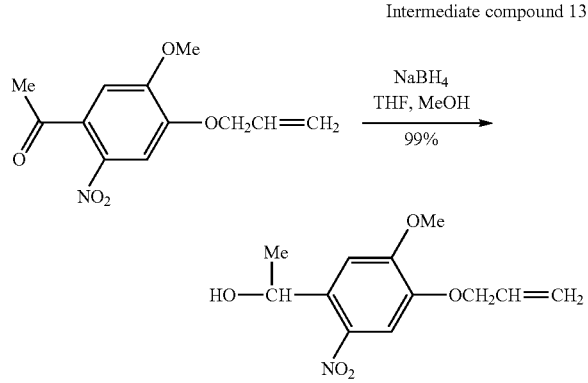

Intermediate compound 13

<<Step 4; Synthesis of 1-(4-allyloxy-5-methoxy-2-nitrophenyl)ethyl N-succinimidyl carbonate>>

The intermediate compound 13 (2.50 g, 9.85 mmol) was put into a 200 mL two-necked eggplant flask to be dissolved in dry acetonitrile (35 mL), di(N-succinimidyl)carbonate (6.36 g, 24.8 mmol) and trimethylamine (4.05 g, 40.1 mmol) were added thereto, and the solution was stirred at room temperature for 17 hours in a nitrogen atmosphere. After concentration, chloroform (150 mL, 60 mL×2), pure water (200 mL), and 2 N hydrochloric acid (10 mL) were added to the resulting solution for extraction, and the organic layer was washed with saturated saline solution (100 mL×3), dried over anhydrous magnesium sulfate, filtered, and concentrated. The resultant was purified by silica gel column chromatography (hexane:ethyl acetate=2:1), thereby obtaining 2.97 g (7.54 mmol, 77%) of a yellowish white solid (intermediate compound 14; 1-(4-allyloxy-5-methoxy-2-nitrophenyl)ethyl N-succinimidyl carbonate).

The identification result of the obtained intermediate compound 14 is described below.

$^1$H NMR (CDCl$_3$/TMS, 400 MHz): δ 1.76 (3H, d, J=6.4 Hz), 2.80 (4H, s), 4.06(3H, s), 4.67 (2H, dt, J=5.5, 1.4 Hz), 5.37 (1H, dq, J=11, 1.3 Hz), 5.47 (1H, dq, J=17, 1.5 Hz), 6.07 (1H, ddt, J=17, 11, 5.4 Hz), 6.51 (1H, q, J=6.4 Hz), 7.08 (1H, s), 7.65 (1H, s).

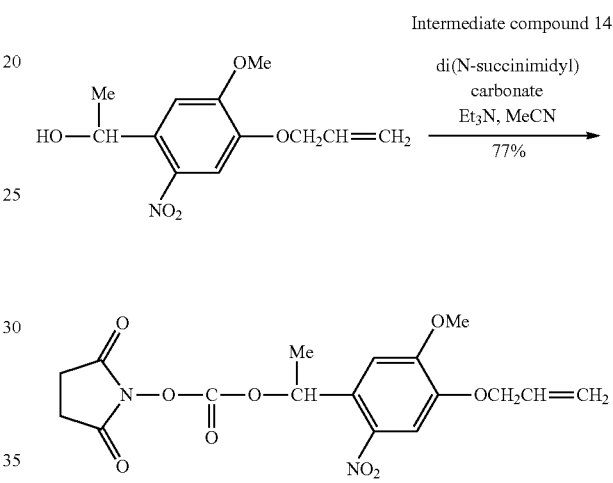

Intermediate compound 14

In the present example, the intermediate compound 14 was synthesized according to the above-described method, but an intermediate compound 14 synthesized according to, for example, the method described in H. Nakayama et al., Colloids Surf. B, 2010, 76, p. 88 to 97 may also be used.

<<Step 5; Synthesis of 1-(5-methoxy-2-nitro-4-(3-tris(trimethylsiloxy)silylpropoxy)phenyl)ethyl N-succinimidyl carbonate>>

The intermediate compound 14 (300 mg, 0.761 mmol) was put into a 30 mL two-necked eggplant flask to be dissolved in dry tetrahydrofuran (6 mL), tris(trimethylsiloxy)silane (677 mg, 2.28 mmol) and a Karstedt catalyst (5 drops) were added thereto, and the solution was stirred at room temperature for 20 minutes in a nitrogen atmosphere. After concentration, the resultant was purified by silica gel column chromatography (hexane:ethyl acetate:tetramethoxysilane=60:20:1→50:50:1), thereby obtaining 281 mg (0.407 mmol, 53%) of a yellow viscous material (compound 1a; 1-(5-methoxy-2-nitro-4-(3-tris(trimethylsiloxy)silylpropoxy)phenyl)ethyl N-succinimidyl carbonate).

The identification result of the obtained compound 1a is described below.

$^1$H NMR (CDCl$_3$/TMS, 400 MHz): δ 0.10 (27H, s), 0.55-0.60 (2H, m), 1.76 (3H, d, J=6.5 Hz), 1.85-1.94 (2H, m), 2.80 (4H, s), 3.98-4.03 (2H, m), 4.04 (3H, s), 6.51 (1H, q, J=6.4 Hz), 7.07 (1H, s), 7.62 (1H, s).

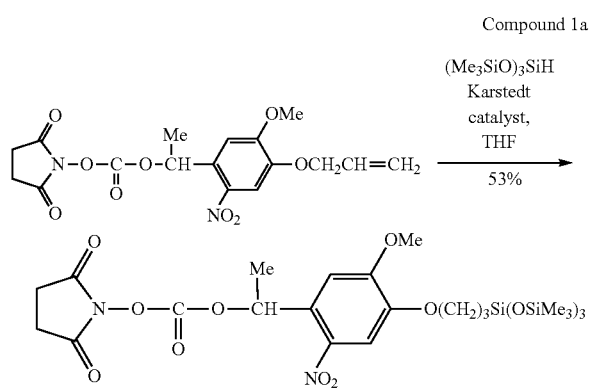

Compound 1a

<Synthesis of Compound 1b>
<<Synthesis of Intermediate Compound 13>>
An intermediate compound 13 was synthesized according to the same method as those for <Synthesis of compound 1a> <<Steps 1 to 3>> described above.

<<Intermediate Compound 15; Synthesis of 1-(4-(3-(1,1,3,3,5,5,5-heptamethyltrisiloxanyl)propoxy)-5-methoxy-2-nitrophenyl)ethanol>>

The intermediate compound 13 (512 mg, 2.02 mmol) was put into a 100 mL two-necked eggplant flask to be dissolved in dry tetrahydrofuran (10 mL), 1,1,3,3,5,5,5-heptamethyltrisiloxane (1.36 g, 6.09 mmol) and a Karstedt catalyst (5 drops) were added thereto, and the solution was stirred at room temperature for 18 hours in a nitrogen atmosphere. After concentration, the resultant was purified by silica gel column chromatography (hexane:ethyl acetate=15:1, 1% tetramethoxysilane), thereby obtaining 627 mg (1.02 mmol, 50%) of a yellow viscous material (intermediate compound 15; 1-(4-(3-(1,1,3,3,5,5,5-heptamethyltrisiloxanyl) propoxy)-5-methoxy-2-nitrophenyl)ethanol).

The identification result of the obtained intermediate compound 15 is described below.

$^1$H NMR (CDCl$_3$/TMS, 400 MHz): δ 0.03 (6H, s), 0.08 (9H, s), 0.12 (6H, s), 0.63-0.68 (2H, m), 1.56 (3H, d, J=6.2 Hz), 1.86-1.95 (2H, m), 2.28 (1H, d, J=3.7 Hz), 3.99 (3H, s), 4.02 (2H, t, J=7.2 Hz), 5.52-5.60 (1H, m), 7.29 (1H, s), 7.56 (1H, s).

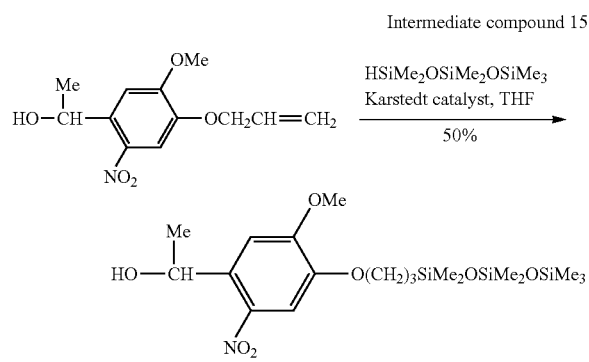

Intermediate compound 15

<<Compound 1b; Synthesis of 1-(4-(3-(1,1,3,3,5,5,5-heptamethyltrisiloxanyl)propoxy)-5-methoxy-2-nitrophenyl) ethyl N-succinimidyl carbonate>>

The intermediate compound 15 (618 mg, 1.30 mmol) was put into a 30 mL two-necked eggplant flask to be dissolved in dry acetonitrile (11 mL), di(N-succinimidyl)carbonate (860 mg, 3.36 mmol) and trimethylamine (540 mg, 5.34 mmol) were added thereto, and the solution was stirred at room temperature for 18 hours in a nitrogen atmosphere. After concentration, chloroform (20 mL×3), pure water (30 mL), and 2 N hydrochloric acid (2 mL) were added to the resulting solution for extraction, and the organic layer was washed with saturated saline solution (50 mL×3), dried over anhydrous magnesium sulfate, filtered, and concentrated. The resultant was purified by silica gel column chromatography (hexane:ethyl acetate=5:1, 1% tetramethoxysilane), thereby obtaining 326 mg (0.529 mmol, 41%) of a yellow viscous material (compound 1b; 1-(4-(3-(1,1,3,3,5,5,5-heptamethyltrisiloxanyl)propoxy)-5-methoxy-2-nitrophenyl) ethyl N-succinimidyl carbonate).

The identification result of the obtained compound 1b is described below.

$^1$H NMR (CDCl$_3$/TMS, 400 MHz): δ 0.03 (6H, s), 0.09 (9H, s), 0.12 (6H, s), 0.62-0.69 (2H, m), 1.76 (3H, d, J=6.4 Hz), 1.86-1.95 (2H, m), 2.80 (4H, s), 3.99-4.05 (2H, m), 4.04 (3H, s), 6.51 (1H, q, J=6.4 Hz), 7.07 (1H, s), 7.63 (1H, s).

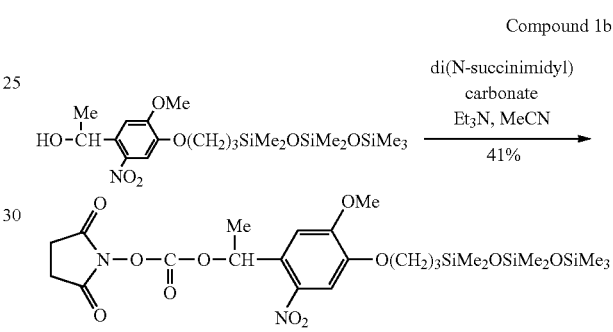

Compound 1b

<Synthesis of Compound 2a>
<<Step 1; Synthesis of 1-(4,5-(methylenedioxy)-2-nitrophenyl)ethanone>>

3,4-(Methylenedioxy)acetophenone (5.04 g, 30.7 mmol) was put into a 200 mL two-necked eggplant flask to be dissolved in trifluoroacetic acid (50 mL), sodium nitrite (6.30 g, 91.4 mmol) was gradually added thereto, and the solution was stirred for 20 hours. Pure water (100 mL) was added thereto for extraction using dichloromethane (100 mL×3), and the organic layer was washed with saturated saline solution (100 mL×3), dried over anhydrous magnesium sulfate, filtered, and concentrated. The resultant was purified by silica gel column chromatography (hexane:ethyl acetate=4:1), thereby obtaining 2.35 g (11.2 mmol, 36%) of a yellow solid (intermediate compound 21; 1-(4,5-(methylenedioxy)-2-nitrophenyl)ethanone).

The identification result of the obtained intermediate compound 21 is described below.

$^1$H NMR (CDCl$_3$/TMS, 400 MHz): δ 2.49 (3H, s), 6.18 (2H, s), 6.75 (1H, s), 7.55 (1H, s).

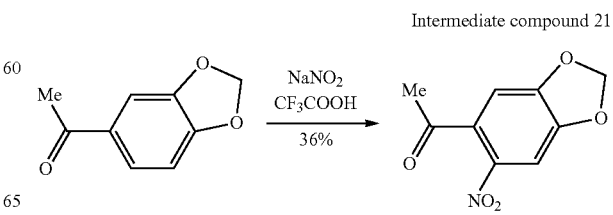

Intermediate compound 21

<<Step 2; Synthesis of 1-(4,5-dihydroxy-2-nitrophenyl)ethanone>>

AlCl₃ (6.55 g, 49.1 mmol) and dichloromethane (48.2 mL) were put into a 300 mL two-necked eggplant flask to obtain a suspension, the suspension was cooled to 0° C., the intermediate compound 21 (3.00 g, 14.4 mmol) dissolved in dichloromethane (70.2 mL) was slowly added dropwise thereto, and the solution was stirred at −10° C. for 2 hours in a nitrogen atmosphere. Next, cold water (98 mL) was added thereto, and the resulting solution was stirred at room temperature for 20 hours in a nitrogen atmosphere. Saturated saline solution (100 mL) and 2 N hydrochloric acid (6 mL) were added thereto for extraction using ethyl acetate (100 mL×3), and the organic layer was washed with saturated saline solution (100 mL×3), dried over anhydrous magnesium sulfate, filtered, and concentrated. The obtained crude product was washed with chloroform, suctioned and filtered, and dried in a vacuum, thereby obtaining 1.53 g (7.74 mmol, 54%) of a yellowish green solid (intermediate compound 22; 1-(4,5-dihydroxy-2-nitrophenyl)ethanone).

The identification result of the obtained intermediate compound 22 is described below.

¹H NMR (CD₃OD/TMS, 400 MHz): δ 2.44 (3H, s), 6.78 (1H, s), 7.49 (1H, s).

Intermediate compound 22

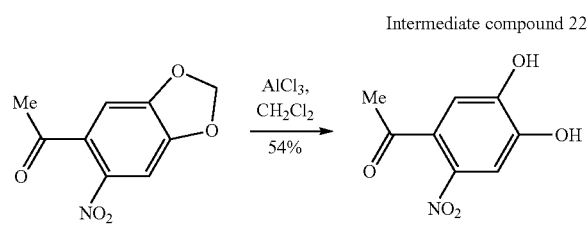 [SMILES: CC(=O)c1cc2c(cc1[N+](=O)[O-])OCO2 ; CC(=O)c1cc(O)c(O)cc1[N+](=O)[O-]]

<<Step 3; Synthesis of 1-(4,5-diallyloxy-2-nitrophenyl)ethanone>>

The intermediate compound 22 (1.03 g, 5.21 mmol) was put into a 100 mL two-necked eggplant flask to be dissolved in acetone (10 mL), potassium carbonate (2.88 g, 20.8 mmol) was added thereto, the solution was stirred at room temperature for 30 minutes, allyl bromide (2.98 g, 24.6 mmol) was added thereto, and the resulting solution was refluxed for 2.5 hours. After concentration, ethyl acetate (100 mL×3) and pure water (100 mL) were added to the resulting solution for extraction, and the organic layer was washed with saturated saline solution (100 mL×2), dried over anhydrous magnesium sulfate, filtered, and concentrated, thereby obtaining 1.27 g (4.59 mmol, 88%) of a pale yellow solid (intermediate compound 23; 1-(4,5-diallyloxy-2-nitrophenyl)ethanone).

The identification result of the obtained intermediate compound 23 is described below.

¹H NMR (CDCl₃/TMS, 400 MHz): δ 2.49 (3H, s), 4.68-4.72 (4H, m), 5.35-5.40 (2H, m), 5.42-5.51 (2H, m), 6.00-6.12 (2H, m), 6.76 (1H, s), 7.62 (1H, s).

Intermediate compound 23

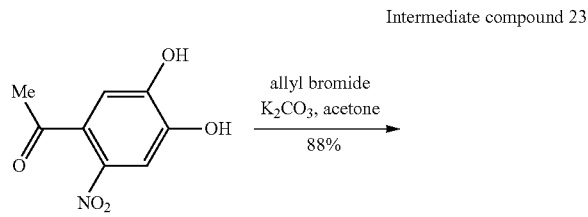

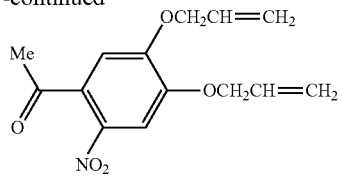

<<Step 4; Synthesis of 1-(4,5-diallyloxy-2-nitrophenyl)ethanol>>

The intermediate compound 23 (1.09 g, 3.94 mmol) was put into a 200 mL eggplant flask to be dissolved in tetrahydrofuran (5.0 ml), methanol (5.0 mL) was added thereto, sodium borohydride (0.52 g, 13.9 mmol) was added thereto on an ace bath, and the solution was stirred at 0° C. for 1 hour. After concentration, ethyl acetate (100 mL×3), pure water (100 mL), and 2 N hydrochloric acid (5 mL) were added to the resulting solution for extraction, and the organic layer was washed with saturated saline solution (100 mL×3), dried over anhydrous magnesium sulfate, filtered, and concentrated. The obtained crude product was washed with hexane, suctioned and filtered, and dried in a vacuum, thereby obtaining 0.90 g (3.22 mmol, 82%) of a yellow solid (intermediate compound 24; 1-(4,5-diallyloxy-2-nitrophenyl)ethanol).

The identification result of the obtained intermediate compound 24 is described below.

¹H NMR (CDCl₃/TMS, 400 MHz): δ 1.54 (3H, d, J=6.3 Hz), 2.27 (1H, d, J=3.6 Hz), 4.64-4.76 (4H, m), 5.32-5.38 (2H, m), 5.42-5.50 (2H, m), 5.51-5.57 (1H, m), 6.02-6.13 (2H, m), 7.30 (1H, s), 7.59 (1H, s).

Intermediate compound 24

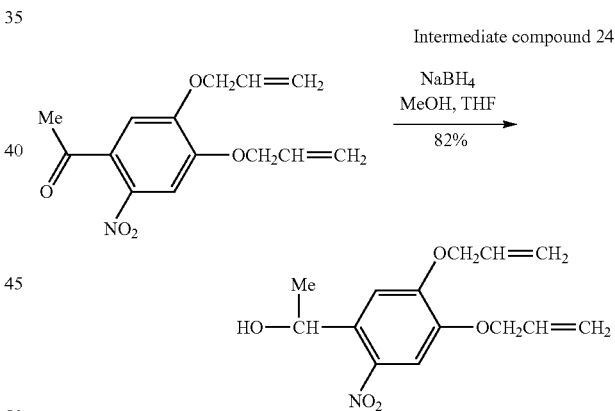

<<Step 5; Synthesis of 1-(4,5-diallyloxy-2-nitrophenyl)ethyl N-succinimidyl carbonate>>

The intermediate compound 24 (0.80 g, 2.87 mmol) was put into a 100 mL two-necked eggplant flask to be dissolved in dry acetonitrile (10.0 mL), di(N-succinimidyl)carbonate (1.25 g, 4.90 mmol) and trimethylamine (0.904 g, 8.93 mmol) were added thereto, and the solution was stirred at room temperature for 19 hours in a nitrogen atmosphere. After concentration, ethyl acetate (100 mL×3), pure water (100 mL), and 2 N hydrochloric acid (5 mL) were added to the resulting solution for extraction, and the organic layer was washed with saturated saline solution (100 mL×3), dried over anhydrous magnesium sulfate, filtered, and concentrated. The resultant was purified by silica gel column chromatography (hexane:ethyl acetate=4:1→2:1), thereby obtaining 0.846 g (2.01 mmol, 70%) of a yellowish white solid (intermediate compound 25; 1-(4,5-diallyloxy-2-nitrophenyl)ethyl N-succinimidyl carbonate).

The identification result of the obtained intermediate compound 25 is described below.

$^1$H NMR (CDCl$_3$/TMS, 400 MHz): δ 1.74 (3H, d, J=6.4 Hz), 2.80 (4H, s), 4.65-4.69 (2H, m), 4.73-4.86 (2H, m), 5.33-5.41 (2H, m), 5.43-5.54 (2H, m), 6.01-6.16 (2H, m), 6.50 (1H, q, J=6.4 Hz), 7.10 (1H, s), 7.65 (1H, s).

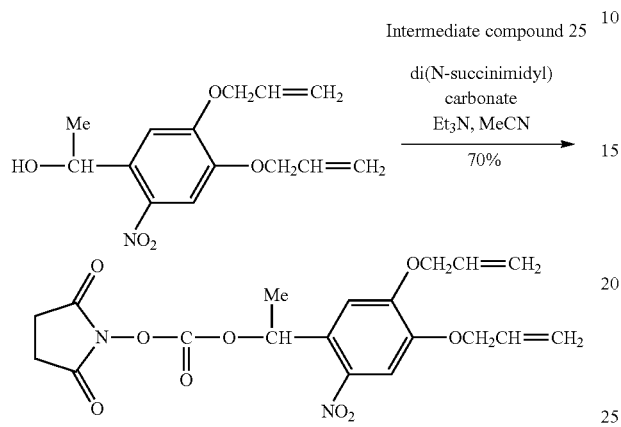

<<Step 6; Synthesis of 1-(2-nitro-4,5-bis(3-tris(trimethylsiloxy)silylpropoxy)phenyl)ethyl N-succinimidyl carbonate>>

The intermediate compound 25 (0.426 g, 1.01 mmol) was put into a 30 mL two-necked eggplant flask to be dissolved in dry tetrahydrofuran (7.0 mL), tris(trimethylsiloxy)silane (1.21 g, 4.09 mmol) and a Karstedt catalyst (10 drops) were added thereto, and the solution was stirred at room temperature for 24 minutes in a nitrogen atmosphere. After concentration, the resultant was purified by silica gel column chromatography (hexane:ethyl acetate:tetramethoxysilane=8:1, 1% tetramethoxysilane), thereby obtaining 0.11 g (0.11 mmol, 11%) of a yellow viscous material (compound 2a; 1-(2-nitro-4,5-bis(3-tris(trimethylsiloxy)silylpropoxy)phenyl)ethyl N-succinimidyl carbonate).

The identification result of the obtained compound 2a is described below.

$^1$H NMR (CDCl$_3$/TMS, 400 MHz): δ 0.10-0.11 (54H, m), 0.54-0.65 (4H, m), 1.75 (3H, d, J=6.4 Hz), 1.83-1.97 (4H, m), 2.80 (4H, s), 3.97-4.17 (4H, m), 6.52 (1H, q, J=6.6 Hz), 7.05 (1H, s), 7.61 (1H, s).

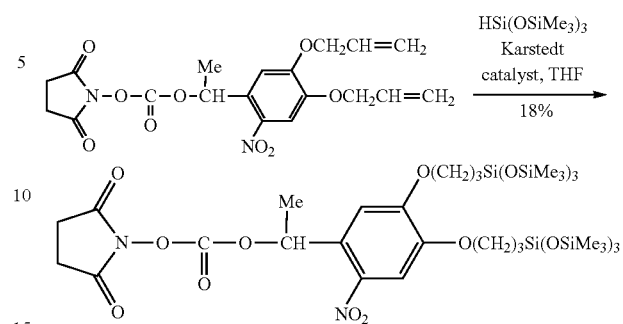

<Synthesis of Compound 2b>

<<Synthesis of Intermediate Compound 25>>

An intermediate compound 25 was synthesized according to the same method as that for <Synthesis of compound 2a>described above.

<<Compound 2b; Synthesis of 1-(4,5-bis(3-(1,1,3,3,5,5,5-heptamethyltrisiloxanyl)propoxy)-2-nitrophenyl)ethyl N-succinimidyl carbonate>>

The intermediate compound 25 (0.31 g, 0.75 mmol) was put into a 20 mL two-necked eggplant flask to be dissolved in dry tetrahydrofuran (6.0 mL), 1,1,3,3,5,5,5-heptamethyltrisiloxane (0.66 g, 2.98 mmol) and a Karstedt's catalyst (10 drops) were added thereto, and the solution was stirred at room temperature for 2.5 hours in a nitrogen atmosphere. After concentration, the resultant was purified by silica gel column chromatography (hexane:ethyl acetate=10:1, 1% tetramethoxysilane), thereby obtaining 0.15 g (0.17 mmol, 23%) of a yellow viscous material (compound 2b; 1-(4,5-bis(3-(1,1,3,3,5,5,5-heptamethyltrisiloxanyl)propoxy)-2-nitrophenyl)ethyl N-succinimidyl carbonate).

The identification result of the obtained compound 2b is described below.

$^1$H NMR (CDCl$_3$/TMS, 400 MHz): δ 0.03 (6H, s), 0.04 (6H, s), 0.08 (9H, s), 0.09 (9H, s), 0.12 (6H, s), 0.12 (6H, s), 0.63-0.73 (4H, m), 1.75 (3H, d, J=6.4 Hz), 1.84-1.96 (4H, m), 2.80 (4H, s), 3.97-4.21 (4H, m), 6.48-6.55 (1H, m), 7.05 (1H, s), 7.61 (1H, s).

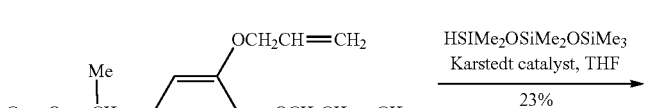

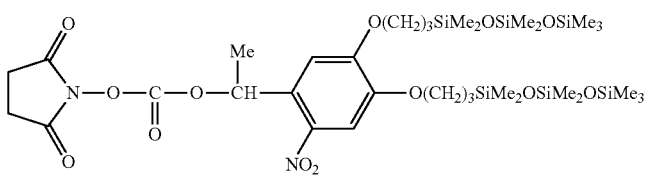

<Synthesis of Compound 2c>
<<Synthesis of Intermediate Compound 25>>
An intermediate compound 25 was synthesized according to the same method as that for <Synthesis of compound 2a>described above.
<<Compound 2c; Synthesis of 1-(4,5-bis(3-(polydimethylsiloxanyl)propoxy)-2-nitrophenyl)ethyl N-succinimidyl carbonate>>
The intermediate compound 25 (49.8 mg, 0.12 mmol) was put into a 20 mL two-necked eggplant flask to be dissolved in dry tetrahydrofuran (3.0 mL), polydimethylsiloxane (2.51 g, 0.31 mmol) and a Karstedt's catalyst (5 drops) were added thereto, and the solution was stirred at room temperature for 16.5 hours in a nitrogen atmosphere. After concentration, 3.23 g of a crude product (compound 2c, 1-(4,5-bis(3-(polydimethylsiloxanyl)propoxy)-2-nitrophenyl)ethyl N-succinimidyl carbonate) was obtained.

$^1$H NMR (CDCl$_3$/TMS, 400 MHz): δ 0.01-0.20 (1288H, m), 0.61-0.75 (4H, m), 0.96 (6H, t, J=7.6 Hz), 1.25-1.41 (8H, m), 1.75 (3H, d, J=6.4 Hz), 1.82-2.00 (4H, m), 2.79 (4H, s), 3.95-4.22 (4H, m), 6.44-6.56 (1H, m), 7.05 (1H, s), 7.61 (1H, s).

The identification result of the obtained compound 2c is described below.

$^1$H NMR (CDCl$_3$/TMS, 400 MHz): δ 0.01-0.20 (1288H, m), 0.61-0.75 (4H, m), 0.96 (6H, t, J=7.6 Hz), 1.25-1.41 (8H, m), 1.75 (3H, d, J=6.4 Hz), 1.82-2.00 (4H, m), 2.79 (4H, s), 3.95-4.22 (4H, m), 6.44-6.56 (1H, m), 7.05 (1H, s), 7.61 (1H, s).

temperature for 18 hours in a nitrogen atmosphere. The substrate was rinsed with methanol and chloroform and then dried in a nitrogen flow (the following step 2).

The modified substrate was irradiated with light having a wavelength of 365 nm and an illuminance of 15 J (set to 60 J only in a case of the compound 2c) through a filter in air using an ultrahigh mercury lamp. The substrate was ultrasonically washed with chloroform for 5 minutes and dried using a nitrogen flow (the following step 3).

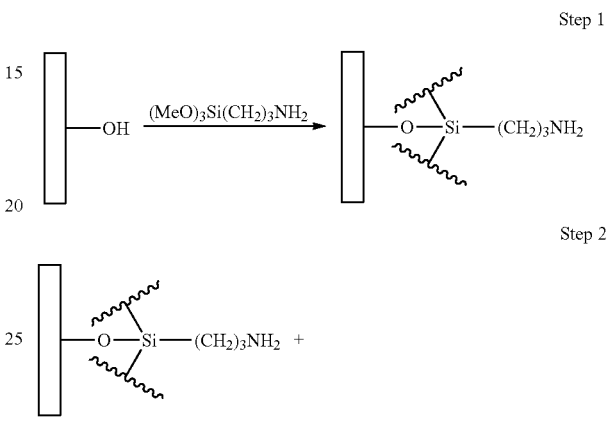

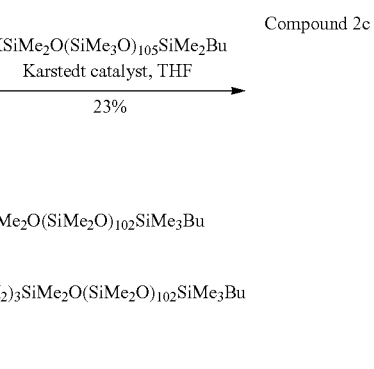

Compound 2c

<Surface Modification>
A silicon wafer provided with a thermal oxide film (SiO$_2$/Si substrate) was ultrasonically washed for 5 minutes with pure water, acetone, methanol, and chloroform respectively, dried in a nitrogen flow, and subjected to a pretreatment by being irradiated with UV for 1 hour using a UV-ozone cleaner.

Next, 3-aminopropyltrimethoxysilane was dissolved in dry toluene to prepare a 0.1 mM solution, and the substrate which had been subjected to the pre-treatment was put into the solution and immersed therein at room temperature for 1 hour in a nitrogen atmosphere. The substrate was ultrasonically washed with methanol and chloroform for 5 minutes and dried using a nitrogen flow (the following step 1).

Next, each 1.0 mM solution was prepared by dissolving each of the compounds 1a, 1b, 2a, and 2b obtained by the above-described method in acetonitrile and dissolving the compound 2c in toluene. Further, trimethylamine (3.0 mM) was added thereto, and the above-described aminated substrate was put into the solution and immersed therein at room temperature for

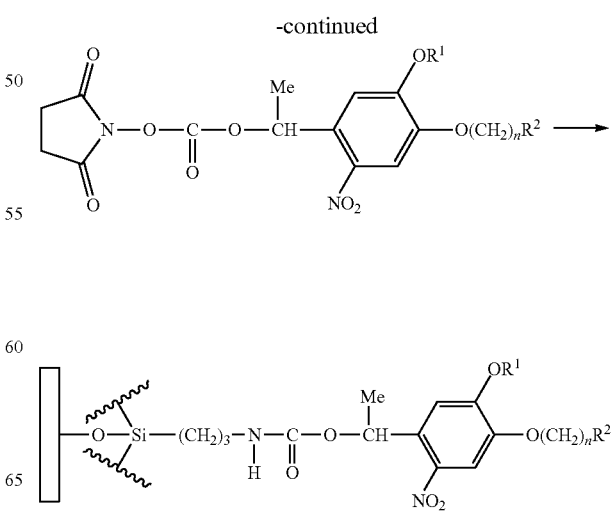

-continued

Step 3

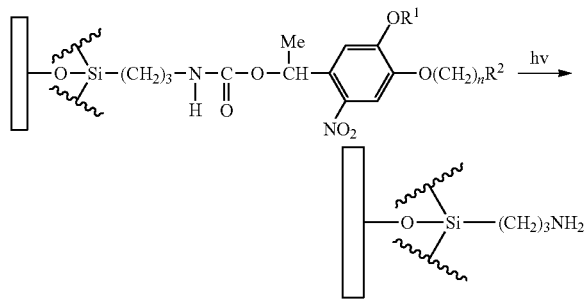

<Measurement of Contact Angle>

The static contact angle of water before and after irradiation with light was measured using a contact angle meter (Kyowa Interface Science, Inc.) according to a liquid droplet method and a θ/2 method. The static contact angle was measured using water, diiomethane, or 1-bromonaphthalene as the probe liquid. The results are listed in Table 1. In Table 1, "$(MeO)_3Si(CH_2)_3NH_2$" indicates immediately after the step 1, "before irradiation with light" indicates immediately after the step 2, and "after irradiation with light" indicates immediately after the step 3.

TABLE 1

| Modifier | Irradiation with | Contact angle (° C.) | | |
|---|---|---|---|---|
| $SiO_2$/Si substrate | light (15 J) | Water | Diiodomethane | 1-Bromonaphthalene |
| $(MeO)_3Si(CH_2)_3NH_2$ | Not available | 59.4 ± 2.9 | 36.6 ± 1.1 | 23.4 ± 1.3 |
| 1a | Before | 94.3 ± 0.3 | 58.3 ± 0.9 | 52.0 ± 0.5 |
| 1a | After | 71.4 ± 3.6 | 45.5 ± 0.7 | 37.4 ± 1.3 |
| 1b | Before | 80.2 ± 1.1 | 44.3 ± 1.4 | 36.4 ± 0.8 |
| 1b | After | 53.5 ± 1.1 | 37.5 ± 1.6 | 26.6 ± 0.5 |
| 2a | Before | 99.2 ± 0.5 | 63.2 ± 1.4 | 57.4 ± 0.8 |
| 2a | After | 62.9 ± 1.6 | 44.9 ± 1.9 | 37.7 ± 1.1 |
| 2b | Before | 92.4 ± 0.5 | 55.7 ± 1.3 | 51.1 ± 2.3 |
| 2b | After | 57.8 ± 3.1 | 42.5 ± 0.7 | 34.8 ± 0.5 |
| 2c | Before | 99.4 ± 1.0 | 65.3 ± 0.9 | 60.5 ± 1.5 |
| 2c | After (60 J) | 74.2 ± 2.9 | 48.3 ± 2.1 | 42.4 ± 3.3 |

Based on the results listed in Table 1, it was confirmed that the contact angles of all compounds free from fluorine after irradiation with light were decreased.

In the siloxane structure, in a case where the branched compound 1a was compared to the linear compound 1b, the contact angle of the branched compound 1a before and after irradiation with light was greater than of the contact angle of the linear compound 1b.

Further, in a case where the monosubstituted compound 1a was compared to the disubstituted compound 2a, the contact angle of the disubstituted compound 2a was greater than of the contact angle of the monosubstituted compound 1a.

Further, the contact angle of the disubstituted chain-like compound 2c with diiodomethane or 1-bromonaphthalene was the largest before irradiation with light.

REFERENCE SIGNS LIST

S: substrate
CONT: control unit
Sa: surface to be treated
2: substrate supply unit
3: substrate treatment unit
4: substrate recovery unit
6: compound coating unit
7: exposure unit
8: mask
9: patterned material coating unit
100: substrate treatment device

The invention claimed is:
1. A compound represented by Formula (1):

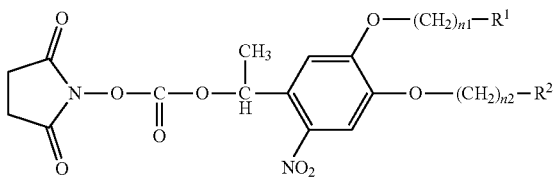

wherein, in the Formula (1), $R^1$ represents any one group selected from an alkyl group having 1 to 5 carbon atoms, a group represented by Formula (R2-1), and a group represented by Formula (R2-2), $R^2$ represents a group represented by the Formula (R2-1) or the Formula (R2-2), n1 represents an integer of 0 to 5, and n2 represents a natural number of 1 to 5:

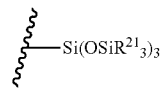

(R2-1)

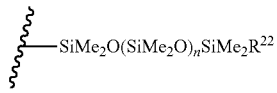

(R2-2)

wherein, in the Formulae (R2-1) and (R2-2), $R^{21}$ and $R^{22}$ each independently represents an alkyl group having 1 to 5 carbon atoms, n represents a natural number, and the wavy line represents a bonding site.

2. The compound according to claim 1,
wherein $R^{21}$ or $R^{22}$ represents any of a methyl group, an isopropyl group, or a tert-butyl group.

3. A substrate for pattern formation, which has a surface chemically modified by the compound according to claim 1.

4. A photodegradable coupling agent which is formed of the compound according to claim 1.

5. A pattern formation method of forming a pattern on a surface of an object to be treated, comprising:
aminating at least a part of the surface of the object to be treated to form an aminated surface;
chemically modifying the aminated surface using the compound according to claim 1;
irradiating the chemically modified surface to be treated with light in a predetermined pattern to generate a latent image formed of a hydrophilic region and a water-repellent region; and
disposing a pattern forming material in the hydrophilic region or the water-repellent region.

6. The pattern formation method according to claim 5, wherein the predetermined pattern corresponds to a circuit pattern for an electronic device.

7. The pattern formation method according to claim 5, wherein the pattern forming material contains a conductive material, a semiconductor material, or an insulating material.

8. The pattern formation method according to claim 7, wherein the conductive material is formed of a conductive fine particle dispersion liquid.

9. The pattern formation method according to claim 7, wherein the semiconductor material is formed of an organic semiconductor material dispersion liquid.

10. A pattern formation method of forming a pattern on a surface of an object to be treated, comprising:
aminating at least a part of the surface of the object to be treated to form an aminated surface;
chemically modifying the aminated surface using the compound according to claim 1;
irradiating the chemically modified surface to be treated with light in a predetermined pattern to generate a latent image formed of a hydrophilic region and a water-repellent region; and
disposing a catalyst for electroless plating in the hydrophilic region and performing electroless plating.

11. The pattern formation method according to claim 5, wherein the object is a substrate having a flexibility.

12. The pattern formation method according to claim 5, wherein the object is formed of a resin material.

13. The pattern formation method according to claim 5, wherein the light includes light having a wavelength included in a range of 200 nm to 450 nm.

14. A transistor production method of producing a transistor which includes a gate electrode, a source electrode, and a drain electrode, comprising:
forming at least one electrode among the gate electrode, the source electrode, and the drain electrode using the pattern formation method according to claim 5.

* * * * *